US00PP26023P3

(12) United States Plant Patent
Nir

(10) Patent No.: US PP26,023 P3
(45) Date of Patent: Oct. 27, 2015

(54) ***CHAMELAUCIUM* PLANT NAMED 'EARLY OFIR'**

(50) Latin Name: *Chamelaucium uncinatum*
Varietal Denomination: EARLY OFIR

(71) Applicant: Nitzan Nir, Kfar Hess (IL)

(72) Inventor: Nitzan Nir, Kfar Hess (IL)

( * ) Notice: Subject to any disclaimer, the term of this patent is extended or adjusted under 35 U.S.C. 154(b) by 111 days.

(21) Appl. No.: 13/986,494

(22) Filed: May 7, 2013

(65) Prior Publication Data

US 2014/0338081 P1 Nov. 13, 2014

(51) Int. Cl.
*A01H 5/02* (2006.01)

(52) U.S. Cl.
USPC ..... Plt./229
CPC ..... *A01H 5/02* (2013.01)

(58) Field of Classification Search
USPC ..... Plt./229
CPC ..... A01H 5/00
See application file for complete search history.

(56) References Cited

PUBLICATIONS

Imports to Peru (retrieved from GOOGLE SEARCH on Sep. 18, 2014, <http://importstoperu2.blogspot.com/2012/03/13122011.html>).*

* cited by examiner

*Primary Examiner* — Keith O. Robinson
(74) *Attorney, Agent, or Firm* — Cassandra Bright

(57) ABSTRACT

A new and distinct *Chamelaucium* cultivar named 'EARLY OFIR' is disclosed, characterized by short, dark colored leaves and medium sized white colored flowers. The new variety is early blooming. The new variety is a *Chamelaucium*, normally producing cut flower stems, or as a garden or container plant.

1 Drawing Sheet

Latin name of the genus and species: *Chamelaucium uncinatum.*

Variety denomination: 'EARLY OFIR'.

BACKGROUND OF THE INVENTION

The new *Chamelaucium* cultivar is a product of chance discover by the inventor, Nitzan Nir, in Kfar Hess, Israel. The new variety was discovered as a seedling growing in a field of various *Chamelaucium uncinatum* varieties during January of 2009, at a commercial nursery in Kfar Hess, Israel. As the variety was discovered as a chance seedling, the parents are unknown.

Asexual reproduction of the new cultivar has been performed by vegetative cuttings. This was first performed at a commercial nursery in Kfar Hess, Israel in November of 2009 and has shown that the unique features of this cultivar are stable and reproduced true to type in successive generations.

SUMMARY OF THE INVENTION

The cultivar 'EARLY OFIR' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'EARLY OFIR'. These characteristics in combination distinguish 'EARLY OFIR' as a new and distinct *Chamelaucium* cultivar:

1. Short leaves.
2. Dark leaf color.

3. Early blooming season beginning in December in the Northern Hemisphere.
4. White flower.
5. Medium flower size.
6. Light yellow flower bud.

COMMERCIAL COMPARISON

Plants of the new cultivar 'EARLY OFIR' are comparable to the variety *Chamelaucium uncinatum* 'Ofir', unpatented. The two *Chamelaucium* varieties are similar in most horticultural characteristics; however, the new variety 'EARLY OFIR' begins flowering approximately 2 months earlier than 'Ofir'. Additionally, flower buds of 'Early OFIR' are Yellow-Green, whereas flower buds of 'Ofir' are white. Additionally, plants of 'Ofir' produce approximately 20% more lateral branches than plants of 'Early Ofir'.

Plants of the new cultivar 'EARLY OFIR' can also be compared to the commercial variety *Chamelaucium uncinatum* 'Alba', unpatented. These varieties are similar in most horticultural characteristics; however 'EARLY OFIR' flowers earlier and produces shorter, darker colored foliage.

BRIEF DESCRIPTION OF THE PHOTOGRAPH

The accompanying photograph in FIG. 1 illustrates in full color a close up of typical flowers and foliage of 'EARLY OFIR'. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'EARLY OFIR' plants grown outdoors in Kfar Hess, Israel. The growing temperature ranged from 15° C. to 35° C. during the day and from −2° C. to 35° C. during the night. General light conditions are bright, normal sunlight. Measurements and numerical values represent averages of typical plant types.

Botanical classification: *Chamelaucium uncinatum* 'EARLY OFIR'.

Age of plant described: A mature plant, at least 2 months old from a rooted cutting.

Typical flowering stems harvested per plant: 120 during the course of the season.

Vase life of flowers: Two weeks.

PROPAGATION

Time to produce a rooted plantlet: 30 to 60 days at approximately 24° C.

Root description: Fibrous.

PLANT

Growth habit: Upright plant produces multiple stems from a pinch, or after harvesting stems.

Height: Approximately 200 cm.

Plant spread: Approximately 80 cm.

Growth rate: Rapid.

Branching characteristics: Moderate branching occurs after pinching.

Length of primary lateral branches: 60 cm on average.

Diameter of lateral branches: 0.3 cm.

Quantity of primary lateral branches: 120. These are the harvested flowering stems.

Characteristics of primary lateral branches:

- *Form*.—Round.
- *Diameter*.—0.5 cm.
- *Color*.—Near RHS Yellow-Green 152B over Grey-Grown 199A.
- *Texture*.—Smooth.
- *Strength*.—Stems brittle.

Internode length: Ranges from 1.5 to 11 cm.

FOLIAGE

Leaf:

- *Arrangement*.—Opposite.
- *Quantity*.—Approximately 6 leaves, in the 10-15 cm section from the top of the branch.
- *Average length*.—1.6 cm.
- *Average width*.—0.1 cm.
- *Shape of blade*.—Needle.
- *Apex*.—Acute.
- *Base*.—Attenuate.
- *Margin*.—Entire.
- *Texture*.—Glabrous all surfaces.
- *Pubescence*.—None.
- *Aspect*.—Straight, occurring at approximately a 15 to 30 degree angle.
- *Color*.—Young foliage: Near RHS Yellow-Green 144A. Mature foliage: Near RHS Green 137B.
- *Venation*.—Indistinguishable from foliage.
- *Petiole*.—Not present.

FLOWER

Natural flowering season: Plants planted during April through August begin flowering December through February, without a juvenility period in Kfar Hess, Israel. Plants flower continuously under short day conditions.

Days to flowering from rooted cutting: Approximately 60 days.

Inflorescence type: Terminal Panicle.

Individual flower type: Single, rotate 5 petaled with a cone shaped hypanthium. Flowers outwardly facing.

Persistent or self-cleaning: Self-Cleaning.

Lastingness: Up to 14 days in a vase. Approximately 45 to 60 days on the plant.

Typical flowering stem length: Approximately 60 cm.

Persistent or self-cleaning: Self-Cleaning.

Bud:

- *Shape*.—Spherical.
- *Length*.—0.45 cm.
- *Diameter*.—0.45 cm.
- *Color*.—Near RHS Yellow-Green 150D.

Inflorescence size:

- *Diameter*.—Average 18 cm.
- *Length*.—Average 20 cm.

Flower size:

- *Diameter*.—Average 1.7 cm.
- *Length*.—Average 0.7 cm.

Corolla:

- *Petals*.—Arrangement: Rotate, not overlapping. Length: Average 0.5 cm. Diameter: Average 0.5 cm. Quantity: 5. Texture: Smooth. Apex: Obtuse rounded. Base: Fused into a hypanthium.
- *Color*.—When opening: Upper surface: Near RHS White NN155B. Lower surface: Near RHS White NN155B. Fully opened: Upper surface: Near RHS White NN155B. Lower surface: Near RHS White NN155B. Aging: Upper surface: Near RHS White NN155C. Lower surface: Near RHS White NN155C.

Hypanthium:

- *Diameter*.—Average 0.7 cm.
- *Length*.—Average 0.3 cm.
- *Shape*.—Obconical.
- *Color*.—When opening: Inner surface: Near RHS White 155A. Outer surface: Near RHS White 155A. Fully opened: Inner surface: Near RHS White 155A. Outer surface: Near RHS White NN155B. Aging: Inner surface: Near RHS White 155A. Outer surface: Near RHS White 155A.

Calyx/sepals:

- *Quantity per flower*.—Fused into a single, conical structure.
- *Length*.—0.3 cm.
- *Width*.—0.7 cm.
- *Margin*.—Entire, incised approximately 1 mm.
- *Texture*.—Smooth.
- *Color*.—Near RHS Green 137A.

Peduncle: Peduncle consists of the plant stem.

Pedicel:

- *Length*.—0.7 cm.
- *Diameter*.—0.1 cm.

Fragrance: None.

REPRODUCTIVE ORGANS

Stamens:
*Number.*—10.
*Filament length.*—1 mm.
*Filament color.*—Near RHS Yellow-White 158B.
Anthers:
*Shape.*—Oval.
*Length.*—0.25-0.5 mm.
*Width.*—0.3 mm.
*Color.*—Near RHS Yellow-Orange 14D.
Pollen: Not observed to date.
Pistil:
*Number.*—1.
*Length.*—0.5 cm.
*Color.*—Near RHS White 155A.
*Style color.*—Near RHS Yellow 13D.
*Stigma.*—Shape: Round. Color: Near RHS Greyed-Orange 175A. Texture: Glabrous.

OTHER CHARACTERISTICS

Seeds and fruits: Single flower produces one fruit. When the fruit is fertile, it will produce 1 seed, occasionally 2 seeds. Fruit type is a nut, colored near Grey-Brown N199A, seed is unwinged colored approximately 1.5 mm, brown in color, too minute to accurately measure color with R.H.S. chart.
Disease/pest resistance: Neither resistance nor susceptibility to the normal diseases and pests of *Chamelaucium* have been observed to date.
Temperature tolerance: From −2° C. to 35° C.
Drought tolerance: Very good tolerance for drought.

What is claimed is:

1. A new and distinct cultivar of *Chamelaucium* plant named 'EARLY OFIR' as herein illustrated and described.

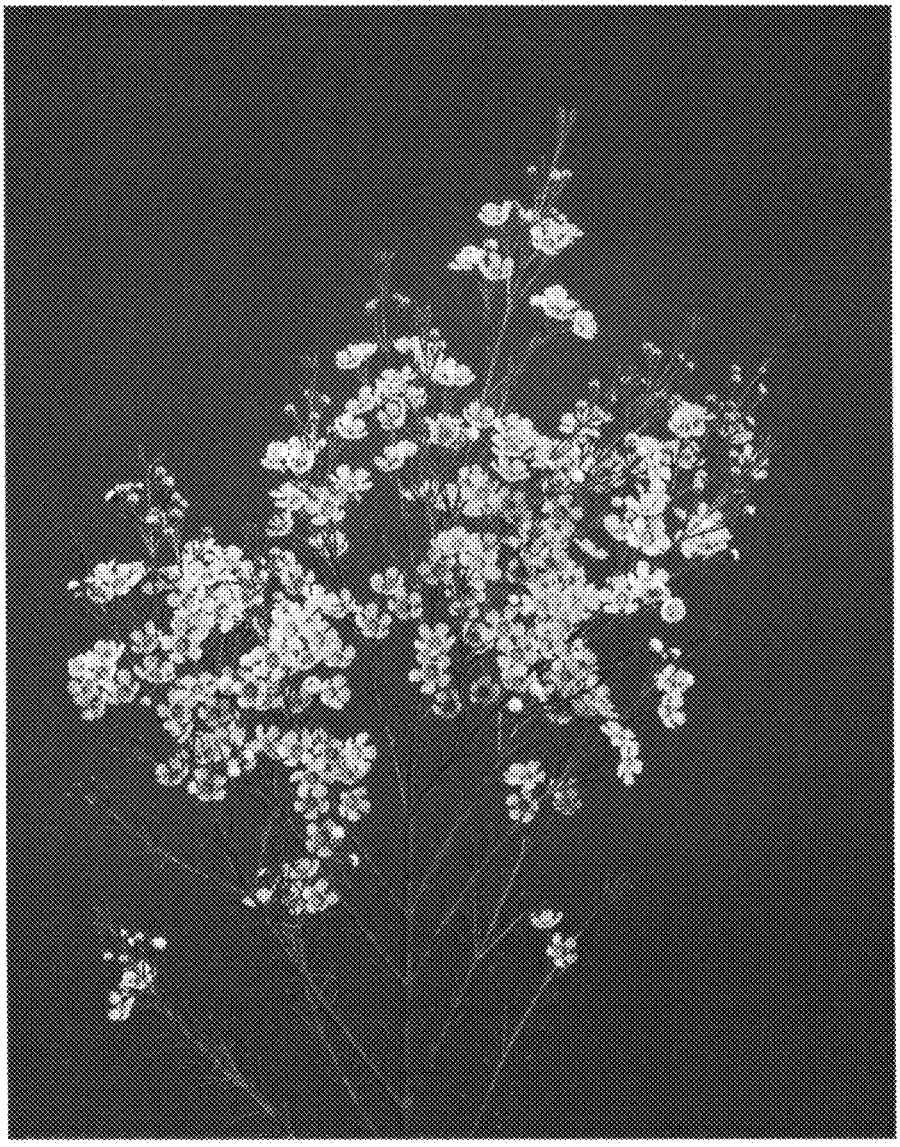

* * * * *